United States Patent [19]

Danree et al.

[11] Patent Number: 4,880,807
[45] Date of Patent: Nov. 14, 1989

[54] NICOTINOYLPIPERAZINES USEFUL FOR TREATMENT OF CONVULSIONS

[75] Inventors: Bernard Danree, Poissy; Michelle Faulques, Courbevoie; Jean-Yves Lacolle, La Celle-Saint-Cloud; Jean-Pierre Riffaud, Versailles, all of France

[73] Assignee: Institut De Recherches Chimiques et Biologiques Appliquees (I.R.C.E.B.A.), Vicq, France

[21] Appl. No.: 281,248
[22] Filed: Dec. 7, 1988

[30] Foreign Application Priority Data

Dec. 16, 1987 [FR] France ................... 8717563

[51] Int. Cl.⁴ ................ A61K 31/505; A61K 31/44; C07D 401/12
[52] U.S. Cl. ................ 514/252; 544/365
[58] Field of Search .......... 544/365; 514/252

[56] References Cited

U.S. PATENT DOCUMENTS 3,865,828  2/1975  Korosi et al. ............ 544/365
3,914,239  10/1975  Kühnis et al. ............ 544/365
4,753,936  6/1988  Franckowiak et al. ...... 544/365

FOREIGN PATENT DOCUMENTS 540697  1/1988  Fed. Rep. of Germany .
2097790  4/1982  United Kingdom .

OTHER PUBLICATIONS

Chemical Abstracts, vol. 108,988, p. 725, No. 150265c, Columbus, Ohio, US; S. Botros et al.: "Synthesis of Certain Pyridinecarboxamides as Potential Antihypertensive Agents" & Egypt. J. Pharm. Sci. 1987, 28(1-4), 405-11.
Guerret et al, CA 98-1073201 (1983).
Yamawaki et al., CA 82-171054t (1975).

*Primary Examiner*—Mukund J. Shah
*Assistant Examiner*—Cecilia Shen
*Attorney, Agent, or Firm*—Burgess, Ryan & Wayne

[57] ABSTRACT

The present invention relates, by way of novel industrial products, to
(i) 4-aryl-1-nicotinoylpiperazines of the formula

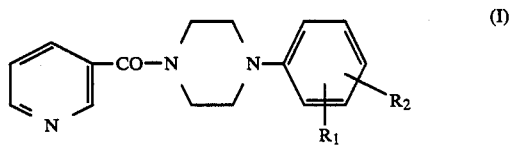

(I)

in which $R_1$ and $R_2$, which can be identical or different, each represent the hydrogen atom, a halogen atom (especially F, Cl or Br) or a $CF_3$, $C_1$-$C_4$-alkyl, $C_1$-$C_4$-alkoxy or $C_2$-$C_4$-acyl group; and
(ii) addition salts thereof.

These products are useful in therapy as anticonvulsants.

16 Claims, No Drawings

NICOTINOYLPIPERAZINES USEFUL FOR TREATMENT OF CONVULSIONS

FIELD OF THE INVENTION

The present invention relates, by way of novel industrial products, to nicotinoylpiperazine derivatives, i.e., more precisely, to the 4-aryl-1-nicotinoylpiperazine compounds of formula I below and to addition salts thereof. It further relates to the method for the preparation of these novel compounds and to their use in therapy as anticonvulsants.

PRIOR ART

It is known that a number of pyridinecarboxamide derivatives have already been described in the past, cf. the summary in Chemical Abstracts 108, 150265c, German patent document C-540 697 and British patent document A-2 097 790.

SUMMARY OF THE INVENTION

According to one of its aspects, the present invention proposes to provide novel compounds belonging to the family of the nicotinoylpiperazines and structurally different from the derivatives of the above-mentioned prior art, which are useful in therapy with regard to their beneficial anticonvulsant properties.

According to another aspect of the invention, a method of preparation appropriate to the synthesis of the said derivatives is recommended.

According to yet another aspect of the invention, a therapeutic composition containing at least one of the said derivatives as the active ingredient is proposed.

The novel derivatives according to the invention, which belong to the family of the nicotinoylpiperazines, are selected from the group consisting of:

(i) 4-aryl-1-nicotinoylpiperazines of the formula

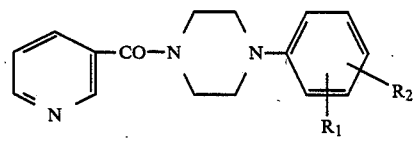

in which $R_1$ and $R_2$, which can be identical or different, each represent the hydrogen atom, a halogen atom (especially F, Cl or Br) or a $CF_3$, $C_1$-$C_4$-alkyl, $C_1$-$C_4$-alkoxy or $C_2$-$C_4$-acyl group; and (ii) addition salts thereof.

DETAILED DESCRIPTION OF THE INVENTION

The invention therefore relates, by way of novel industrial products, to the compounds of formula I and to addition salts thereof.

In the definition of $R_1$ and $R_2$, halogen atoms are understood here to mean fluorine, chlorine and bromine atoms, the preferred halogen atoms for $R_1$ and/or $R_2$ being chlorine and fluorine and the most advantageous from the therapeutic point of view being chlorine.

$C_1$-$C_4$-alkyl and $C_1$-$C_4$-alkoxy groups are understood here to mean groups comprising a saturated hydrocarbon chain which has from 1 to 4 carbon atoms and is linear or branched.

$C_2$-$C_4$-acyl group is understood to mean a group comprising a CO radical bonded to a $C_1$-$C_3$-alkyl radical. The preferred acyl group here is the group $COCH_3$.

From a practical point of view, it is preferable, with regard to the therapeutic efficacy, if $R_1$ and $R_2$ do not both represent the hydrogen atom. $R_1$ and $R_2$, which can be identical or different, will advantageously each represent Cl, F, $CF_3$, $CH_3$, $C_2H_5$, $OCH_3$, $OC_2H_5$ or $COCH_3$, it being possible, if appropriate, for only one of the groups $R_1$ and $R_2$ to represent the hydrogen atom.

Preferably, the group $R_1$ will be located in the 2-position or ortho position of the benzene ring and the group $R_2$ will be located in any one of the other free positions, namely in the 3-, 4-, 5- or 6-position, especially in the meta or para position.

Addition salts are understood here to mean, on the one hand, the acid addition salts obtained by reacting a free base of formula I with a mineral or organic acid, and, on the other hand, the ammonium salts. The following may be mentioned in particular among the acids which can be used to salify the free bases of formula I: hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids. $ICH_3$ and $ClCH_3$ may be mentioned in particular among the compounds which make it possible to obtain ammonium salts. In general, the acid addition salts are preferred to the ammonium salts and, among the said acid addition salts, the hydrochlorides of the compounds of formula I are the preferred substances for therapeutic use as anticonvulsants.

The compounds of formula I can be prepared according to a method known per se by the application of classical reaction mechanisms. The process which is recommended according to the invention consists in reacting an N-arylpiperazine of the formula

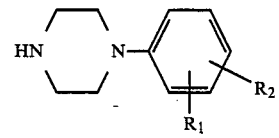

in which $R_1$ and $R_2$ are defined as indicated above, with a nicotinoyl halide of the formula

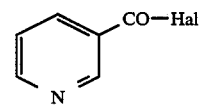

in which Hal represents a halogen atom, especially F, Cl, Br or I. From the point of view of synthesis, the preferred halogen atom is chlorine.

This reaction is advantageously carried out at the reflux temperature of the reaction medium for at least 0.25 h, under substantially stoichiometric conditions (i.e. in proportions of 1 mol of II to about 1 mol of III), in an appropriate solvent. One of the appropriate solvents recommended here is pyridine.

A number of typical compounds according to the invention have been collated in Table I below, without implying a limitation. The melting points which have been mentioned in this Table are instantaneous melting points determined on a Kofler bench. In the said Table, on the one hand Me denotes the methyl group, Et the ethyl group, Ac the acetyl group and AcOEt ethyl acetate, and on the other hand, for the sake of convenience, the group $R_1$ is located in the ortho position and the group $R_2$ in the other positions of the benzene ring.

TABLE I (I)

| Product | Code no. | $R_1$ | $R_2$ | M.p. (°C.) |
|---|---|---|---|---|
| Ex. 1 (a) | B-1 370 | H | 3-CF$_3$ | 238–240 (d) |
| Ex. 2 (a) | B-1 371 | H | 3-Cl | 153–155 |
| Ex. 3 (a) | B-1 372 | 2-Me | 3-Me | 148–150 (e) |
| Ex. 4 (b) | B-1 373 | 2-Cl | H | 98–100 (f) |
| Ex. 5 (c) | B-1 374 | 2-OEt | H | 88–90 (g) |
| Ex. 6 (c) | B-1 230 | H | 3-CF$_3$ | 77–80 (g) |
| Ex. 7 (b) | B-1 368 | H | 4-CF$_3$ | 143–145 (h) |
| Ex. 8 (c) | B-1 273 | 2-F | H | 69–70 (i) |
| Ex. 9 (a) | B-1 252 | 2-F | H | 150–152 (j) |
| Ex. 10 (c) | B-1 247 | H | 4-F | 115–116 (k) |
| Ex. 11 (a) | B-1 251 | H | 4-F | 195–196 (e) |
| Ex. 12 (b) | B-1 363 | 2-CF$_3$ | H | 128–132 (f) |
| Ex. 13 (c) | B-1 275 | 2-Me | H | 134–135 (g) |
| Ex. 14 (a) | B-1 282 | 2-Me | H | 148–150 (h) |
| Ex. 15 (a) | B-1 274 | H | 3-OMe | 174–175 (l) |
| Ex. 16 (a) | B-1 280 | H | 4-OMe | 95–96 (m) |
| Ex. 17 (a) | B-1 295 | H | 4-OMe | 190–192 (l) |
| Ex. 18 (c) | B-1 276 | H | 3-OEt | 106–108 (n) |
| Ex. 19 (a) | B-1 286 | H | 3-OEt | 184–185 (e) |
| Ex. 20 (c) | B-1 271 | H | 4-Ac | 163–164 (o) |
| Ex. 21 (b) | B-1 281 | H | 4-Ac | 178–180 (e) |
| Ex. 22 (c) | B-1 279 | 2-Me | 4-Cl | 113–114 (m) |
| Ex. 23 (b) | B-1 294 | 2-Me | 4-Cl | 165–170 (l) |
| Ex. 24 (c) | B-1 303 | 2-Me | 5-Cl | <50 (p) |
| Ex. 25 (a) | B-1 248 | 2-Me | 5-Cl | 180–182 |
| Ex. 26 (b) | B-1 352 | 2-Me | 6-Cl | 178–180 (j) |
| Ex. 27 (c) | B-1 277 | H | H | 65–66 |
| Ex. 28 (a) | B-1 254 | H | H | 210–212 (l) |
| Ex. 29 (a) | B-1 383 | 2-OEt | H | 184–185 (j) |
| Ex. 30 (b) | B-1 382 | 2-Me | 6-Me | 178–180 (j) |

Notes
(a): dihydrochloride;
(b): monohydrochloride;
(c): free base;
(d): solvent of recrystallization: MeOH
(e): solvent of recrystallization: EtOH
(f): solvent of recrystallization: AcOEt/isopropanol mixture (1/1 v/v)
(g): solvent of recrystallization: AcOEt
(h): solvent of recrystallization: isopropanol
(i): solvent of recrystallization: petroleum ether (fraction boiling at 40–65° C. under normal pressure)
(j): solvent of recrystallization: AcOEt/EtOH mixture (1/1 v/v)
(k): solvent of recrystallization: AcOEt/pentane mixture (1/1 v/v)
(l): solvent of recrystallization: isopropanol/MeOH mixture (1/1 v/v)
(m): solvent of recrystallization: AcOEt/hexane mixture (1/1 v/v)
(n): solvent of recrystallization: AcOEt/cyclohexane mixture (1/1 v/v)
(o): solvent of recrystallization: AcOEt/MeOH mixture (1/1 v/v)
(p): solvent of recrystallization: CH$_2$Cl$_2$/MeOH mixture (1/1 v/v)

The best way of carrying out the invention consists in using 1-nicotinoyl-4-(3-trifluoromethylphenyl)piperazine, 4-(3-chlorophenyl)-1-nicotinoylpiperazine, 4-(4-fluorophenyl)-1-nicotinoylpiperazine, 4-(4-chloro-2-methylphenyl)-1-nicotinoylpiperazine, 4-(5-chloro-2-methylphenyl)-1-nicotinoylpiperazine a addition salts thereof. These products are the most advantageous in therapy with regard to their anticonvulsant properties in particular. The most effective of the said products from the therapeutic point of view are 1-nicotinoyl-4-(3-trifluoromethylphenyl)piperazine (Ex. 6; Code no.: B-1 230) and its dihydrochloride (Ex. 1; Code no.: B-1 370).

The compounds of formula I according to the invention and addition salts thereof are useful in therapy. They behave as anticonvulsant active ingredients and are therefore recommended in the treatment of convulsions and epilepsy in man.

According to the invention, a therapeutic composition is therefore recommended which contains, in association with a physiologically acceptable excipient, at least one compound selected from the 4-aryl-1-nicotinoylpiperazines of formula I and non-toxic addition salts thereof.

Of course, in a composition of this type, the active principle is present in a therapeutically effective amount.

According to the invention, it is recommended to use a substance belonging to the group comprising the 4-aryl-1-nicotinoylpiperazines of formula I and non-toxic addition salts thereof in order to obtain a drug for use in therapy in the treatment of convulsions and especially convulsions of epileptic origin.

PREPARATION I

Preparation of
1-nicotinoyl-4-(3-trifluoromethylphenyl)piperazine (Example 6; Code no.: B-1 230)

600 ml of pyridine and 207.2 g (0.9 mol) of 1-(3-trifluoromethylphenyl)piperazine are introduced into a two-liter three-necked flask provided with a condenser having an H$_2$SO$_4$ bubble counter, a thermometer and a pneumatic stirrer. 127.5 g (0.9 mol) of nicotinoyl chloride are added to the resulting mixture in portions. The reaction medium is refluxed for one hour. After cooling to room temperature (15°–20° C.), it is poured into three liters of iced water, with stirring. The aqueous phase is extracted with 3×300 ml of methylene chloride. The organic phases are combined and washed with 2×250 ml of 5% (w/v) NaHCO$_3$ solution and then to neutrality with 3×250 ml of water. The product phase is dried over sodium sulfate and filtered, the filtrate is collected and the solvent is driven off under vacuum. This gives 287.3 g (yield=95.2%) of a very thick brown liquid which has a gas chromatographic (GC) purity of 99% and shows two spot (1 principal spot + light secondary spot) in thin layer chromatography (TLC) with a CH$_2$Cl$_2$/CH$_3$OH mixture (80/20 v/v) as the mobile phase.

The resulting crude product is purified by fractional distillation under vacuum. 247.8 g (overall yield: 82.1%) of the expected product are collected in the form of an orange oil.

B.p.$_{0.3\ mm\ Hg}$=225°–230° C. (0.3 mm Hg corresponds approximately to 39.9 Pa)
GC purity >99%
TLC: single spot [CH$_2$Cl$_2$/CH$_3$OH (80/20 v/v)]
IR spectrum: conforms to the proposed structure
NMR spectrum: conforms to the proposed structure The resulting oily product is crystallized by the addition of ether. Recrystallization of the resulting crystals from ethyl acetate gives the purified compound B-1 230:
M.p.$_{inst.}$=77°–80° C.

PREPARATION II

Preparation of
1-nicotinoyl-4-(3-trifluoromethylphenyl)piperazine
dihydrochloride (Example 1; Code no.: B-1 370)

247.8 g (0.74 mol) of 1-nicotinoyl-4-(3-trifluoromethylphenyl)piperazine, which has been obtained as indicated in Preparation I, are dissolved in three liters of anhydrous diethyl ether. The resulting solution is cooled and saturated with a stream of dry HCl. The crystals formed are filtered off (especially on a glass frit), washed with anhydrous diethyl ether and then dried under vacuum at 40° C. Recrystallization of these crystals from methanol gives 214.2 g (yield: 70.9%) of B-1 370 in the form of white crystals.

M.p.$_{inst.}$=238°–240° C. TLC=single spot [CH$_2$Cl$_2$/CH$_3$OH/NH$_4$OH (80/2 0/0.5 v/v)]

GC purity >99%

IR spectrum: conforms to the proposed structure

NMR spectrum: conforms to the proposed structure

PHARMACOLOGICAL TESTS

A number of tests undertaken with the compounds according to the invention by comparison with two reference anticonvulsants, namely sodium valproate (abbreviated to VALP) and trimethadione (abbreviated to TRIM), have been summarized below.

I—TOXICITY

The toxicity of the products to be studied was investigated by the oral administration, using an esophageal tube, of each of the said products to male mice with a body weight of 18 to 22 g, divided into groups each containing 10 to 20 animals. The mortality was recorded over a 14-day period.

The results obtained, which are expressed in the form of the LD$_{50}$ in mg/kg, are collated in Table II below.

II—ANTICONVULSANT PROPERTIES

The anticonvulsant properties were investigated on male mice, thirty minutes after the oral administration of the substances to be studied, by the induction of convulsive seizures.

These seizures are caused either by the intraperitoneal injection of pentetrazole (125 mg/kg) or by electrical stimulation of the cornea (supra maximal electroshock, abbreviated to MCE).

The results, expressed in the form of the 50% effective dose (ED$_{50}$) per os (dose protecting 50% of the animals), are collated in Table III below. They show that the products according to the invention exert a protective effect against convulsions which is at least as great as that of the two reference products (VALP and TRIM) when considering the ED$_{50}$ values.

TABLE II

| ORAL TOXICITY IN MICE* | | |
|---|---|---|
| Product | Code no. | LD$_{50}$ (mg/kg) |
| Ex. 1 | B-1 370 | 575 |
| Ex. 2 | B-1 371 | 501 |
| Ex. 3 | B-1 372 | >1000 |
| Ex. 4 | B-1 373 | >1000 |
| Ex. 5 | B-1 374 | 1000 |
| Ex. 6 | B-1 230 | 422 |
| Ex. 7 | B-1 368 | >1000 |
| Ex. 8 | B-1 273 | 1000 |
| Ex. 9 | B-1 252 | >1000 |
| Ex. 10 | B-1 247 | 600 |
| Ex. 11 | B-1 251 | 625 |
| Ex. 12 | B-1 363 | >1000 |
| Ex. 13 | B-1 275 | 1000 |
| Ex. 14 | B-1 282 | >1000 |
| Ex. 15 | B-1 274 | >1000 |
| Ex. 16 | B-1 280 | >1000 |
| Ex. 17 | B-1 295 | >1000 |
| Ex. 18 | B-1 276 | 540 |
| Ex. 19 | B-1 286 | 1000 |
| Ex. 20 | B-1 271 | >1000 |
| Ex. 21 | B-1 281 | >1000 |

TABLE II-continued

| ORAL TOXICITY IN MICE* | | |
|---|---|---|
| Product | Code no. | LD$_{50}$ (mg/kg) |
| Ex. 22 | B-1 279 | 540 |
| Ex. 23 | B-1 294 | >1000 |
| Ex. 24 | B-1 303 | >1000 |
| Ex. 25 | B-1 248 | >1000 |
| Ex. 26 | B-1 352 | >1000 |
| Ex. 27 | B-1 277 | >1000 |
| Ex. 28 | B-1 254 | >1000 |
| Ex. 29 | B-1 383 | ND |
| Ex. 30 | B-1 382 | >1000 |
| VALP | — | 977 |
| TRIM | — | 2182 |

Note
*Toxicity determined on groups each containing 10 to 20 male mice.
ND Non determined

TABLE III

| ANTICONVULSANT PROPERTIES IN MICE* | | | |
|---|---|---|---|
| | | ED$_{50}$ in respect of convulsions induced by: | |
| Product | Code no. | PTZ (mg/kg) | MCE (mg/kg) |
| Ex. 1 | B-1 370 | 17 | 19 |
| Ex. 2 | B-1 371 | 50 | 78 |
| Ex. 3 | B-1 372 | 110 | >200 |
| Ex. 4 | B-1 373 | 160 | 200 |
| Ex. 5 | B-1 374 | >200 | >200 |
| Ex. 6 | B-1 230 | 13 | 20 |
| Ex. 7 | B-1 368 | >200 | >200 |
| Ex. 8 | B-1 273 | 180 | 180 |
| Ex. 9 | B-1 252 | >200 | >200 |
| Ex. 10 | B-1 247 | 62 | 75 |
| Ex. 11 | B-1 251 | 68 | 75 |
| Ex. 12 | B-1 363 | >200 | >200 |
| Ex. 13 | B-1 275 | 161 | 200 |
| Ex. 14 | B-1 282 | 107 | >200 |
| Ex. 15 | B-1 274 | 183 | >200 |
| Ex. 16 | B-1 280 | 120 | >200 |
| Ex. 17 | B-1 295 | 200 | >200 |
| Ex. 18 | B-1 276 | 72 | 118 |
| Ex. 19 | B-1 286 | 142 | 150 |
| Ex. 20 | B-1 271 | >200 | >200 |
| Ex. 21 | B-1 281 | >200 | >200 |
| Ex. 22 | B-1 279 | 55 | 87 |
| Ex. 23° | B-1 294 | 124 | >200 |
| Ex. 24 | B-1 303 | 63 | 83 |
| Ex. 25 | B-1 248 | 79 | 87 |
| Ex. 26 | B-1 352 | >200 | >200 |
| Ex. 27 | B-1 277 | 156 | >200 |
| Ex. 28 | B-1 254 | >200 | >200 |
| Ex. 29 | B-1 383 | ND | ND |
| Ex. 30 | B-1 382 | 138 | ND |
| VALP | — | 244 | 242 |
| TRIM | — | 251 | 500 |

Notes
PTZ: pentetrazole;
MCE: supra maximal electroshock;
*ED$_{50}$ in mg/kg, determined per os on groups each containing ten male mice;
ND: non determined.

III—NEUROTOXIC PROPERTIES

The neurotoxic properties were assessed on male mice by the so-called "Rota-rod" test carried out thirty minutes after the oral administration of the substances to be studied. The animals (divided into groups each containing ten male mice per dose and per product) are installed on the rod and their fall is observed over the next two minutes.

The results obtained are expressed in the form of the 50% neurotoxic dose (TD$_{50}$) per os (dose causing 50% of the animals to fall, expressed in mg/kg). These results are collated in Table IV below, which, for comparison with the above-mentioned reference products (VALP and TRIM), also gives the values of the ratios $TD_{50}/ED_{50}$ (protection index) and $LD_{50}/ED_{50}$ (therapeutic index), in which the $ED_{50}$ values are the 50% effective doses in respect of the convulsions induced by pentetrazole (PTZ) and supra-maximal electroshock (MCE), determined as indicated above (see Table III in particular).

The results in Table IV clearly show that, in particular, the protection indices and therapeutic indices of the compounds according to the invention of Ex. 1 (B-1 370) and Ex. 6 (B-1 230) are better than those of the reference products, namely sodium valproate and trimethadione.

TABLE IV

| | | NEUTROTOXIC ACTIVITY | | | | | |
|---|---|---|---|---|---|---|---|
| Pro-duct | Code no. | $TD_{50}$* (mg/kg) | Protection index | | $LD_{50}$ (mg/kg) | Therapeutic index | |
| | | | PTZ | MCE | | PTZ | MCE |
| Ex. 1 | B-1 370 | 154 | 9.1 | 8.1 | 575 | 33.8 | 30.2 |
| Ex. 6 | B-1 230 | 119 | 9.1 | 6.0 | 422 | 32.5 | 21.1 |
| Ex. 8 | B-1 273 | 500 | 2.8 | 2.8 | 1000 | 5.6 | 5.6 |
| Ex. 13 | B-1 275 | 800 | 4.9 | 4.0 | 1000 | 6.2 | 5.0 |
| Ex. 14 | B-1 282 | 635 | 5.9 | <3.0 | >1000 | >10.0 | <5.0 |
| Ex. 18 | B-1 276 | 291 | 4.0 | 2.5 | 540 | 7.5 | 4.6 |
| Ex. 19 | B-1 286 | 250 | 1.8 | 1.7 | 1000 | 7.0 | 6.7 |
| Ex. 22 | B-1 279 | 300 | 5.4 | 3.4 | 540 | 9.8 | 6.2 |
| Ex. 23 | B-1 294 | 650 | 7.4 | 4.5 | >1000 | >8.1 | <5.0 |
| Ex. 24 | B-1 303 | 525 | 8.3 | 6.3 | >1000 | >15.9 | >12.0 |
| Ex. 25 | B-1 248 | 355 | 4.5 | 4.1 | >1000 | >12.7 | >11.5 |
| VALP | — | 670 | 2.7 | 2.8 | 977 | 4.0 | 4.0 |
| TRIM | — | 1000 | 4.0 | 2.0 | 2182 | 8.7 | 4.4 |

Notes
Protection index: $TD_{50}$ per os/$ED_{50}$ per os
Therapeutic index: $LD_{50}$ per os/$ED_{50}$ per os
*dose determined per os on groups each containing ten male mice.

What is claimed is:

1. A compound belonging to the family of the nicotinoylpiperazines, which is selected from the group consisting of:
   (i) 4-aryl-1-nicotinoylpiperazines of the formula

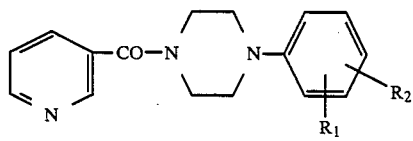

(I)

in which $R_1$ and $R_2$, which can be identical or different, each represent the hydrogen atom, a halogen atom or a $CF_3$, $C_1$-$C_4$-alkyl, $C_1$-$C_4$-alkoxy or $C_2$-$C_4$-acyl group; and
   (ii) a non-toxic addition salt thereof.

2. A compound according to claim 1 wherein the halogen atom within the definition of $R_1$ and $R_2$ is selected from the group consisting of F, Cl and Br.

3. A compound according to claim 1 wherein $R_1$ and $R_2$, which can be identical or different, each represent H, Cl, F, $CF_3$, $C_2H_5$, $OCH_3$, $OC_2H_5$ or $COCH_3$, and only one of the groups $R_1$ and $R_2$ represents a hydrogen atom.

4. A compound according to claim 1 or claim 3 wherein $R_1$ when other than hydrogen is in the 2-position and $R_2$ when other than hydrogen is in the 3-, 4-, 5- or 6-position of the benzene ring.

5. 1-Nicotinoyl-4-(3-trifluoromethylphenyl)piperazine and a non-toxic addition salt thereof.

6. 4-(3-Chlorophenyl)-1-nicotinoylpiperazine and a non-toxic addition salt thereof.

7. 4-(4-Fluorophenyl)-1-nicotinoylpiperazine and a non-toxic addition salt thereof.

8. 4-(4-Chloro-2-methylphenyl)-1-nicotinoylpiperazine and a non-toxic addition salt thereof.

9. 4-(5-Chloro-2-methylphenyl)-1-nicotinoylpiperazine and a non-toxic addition salt thereof.

10. 4-(4-Acetylphenyl)-1-nicotinoylpiperazine and a non-toxic addition salt thereof.

11. A therapeutic composition useful in the treatment of convulsions, said composition being comprised of an anti-convulsive-effective amount of the compound of claim 1 and a physiologically acceptable excipient.

12. A method for the treatment of convulsions which comprises administering an anti-convulsive-effective amount of the therapeutic composition of claim 11.

13. The method of claim 12 wherein the convulsions are of epileptic origin.

14. The method of claim 12 wherein said compound is 1-Nicotinoyl-4-(3-trifluoromethylphenyl)piperazine or a non-toxic addition salt thereof.

15. The method of claim 12 wherein said compound is 4-(3-Chlorophenyl)-1-nicotinoylpiperazine or a non-toxic addition salt thereof.

16. The method of claim 12 wherein said compound is 4-(4-Fluorophenyl)-1-nicotinoylpiperazine or a non-toxic addition salt thereof.

* * * * *